United States Patent [19]
Hays et al.

[11] Patent Number: 5,869,092
[45] Date of Patent: Feb. 9, 1999

[54] PREVENTION OF LEAKAGE AND PHASE SEPARATION DURING THERMOTROPIC PHASE TRANSITION IN LIPOSOMES AND BIOLOGICAL CELLS

[75] Inventors: Lisa M. Hays; John H. Crowe; Lois M. Crowe; Robert E. Feeney; Ann E. Oliver, all of Davis, Calif.

[73] Assignee: The Regents of the University of California, Oakland, Calif.

[21] Appl. No.: 768,148

[22] Filed: Dec. 17, 1996

Related U.S. Application Data

[63] Continuation-in-part of Ser. No. 729,921, Oct. 15, 1996, abandoned, which is a continuation-in-part of Ser. No. 369,193, Jan. 5, 1995, abandoned.

[51] Int. Cl.⁶ .................................................. A61K 9/127
[52] U.S. Cl. ............................................................. 424/450
[58] Field of Search .............................. 424/450; 514/2, 514/12, 21; 428/402.2; 435/243

[56] References Cited

U.S. PATENT DOCUMENTS

| | | |
|---|---|---|
| 5,118,792 | 6/1992 | Warren et al. . |
| 5,173,219 | 12/1992 | Kim . |
| 5,225,182 | 7/1993 | Sharma . |
| 5,358,931 | 10/1994 | Rubinsky et al. . |

OTHER PUBLICATIONS

M.J. Poznansky, et al., "Biological Approaches to the Controlled Delivery of Drugs: A Critical Review," *Pharmacological Reviews* 36(4): 277–335 (1984).

*Primary Examiner*—Gollamudi S. Kishore
*Attorney, Agent, or Firm*—Townsend and Townsend and Crew LLP

[57] ABSTRACT

Leakage from liposomes or biological cells and structural damage, which occur upon cooling through the thermotropic phase transition temperature and upon storage at temperatures below the phase transition temperature are reduced or eliminated by incorporating thermal hysteresis proteins in the liposome or cell structure. Preferred thermal hysteresis proteins are antifreeze proteins and antifreeze glycoproteins from polar fish species, and chromatographic fraction no. 8 of antifreeze glycoproteins has been found to be particularly effective.

15 Claims, 11 Drawing Sheets

5,869,092

PREVENTION OF LEAKAGE AND PHASE SEPARATION DURING THERMOTROPIC PHASE TRANSITION IN LIPOSOMES AND BIOLOGICAL CELLS

CROSS REFERENCE TO RELATED APPLICATION

This application is a continuation-in-part of copending application Ser. No. 08/729,921, filed Oct. 15, 1996 now abandoned, which is a continuation-in-part of copending application Ser. No. 08/369,193, filed Jan. 5, 1995 now abandoned. The entire contents of both applications are incorporated herein by reference.

GOVERNMENT RIGHTS

This invention was made at least in part with United States Government support under Grant Nos. IBN 93-08581 and DCB89-18822, awarded by the National Science Foundation, and Grant No. N00014-94-1-0379, awarded by the Office of Naval Research. The United States Government has certain rights in this invention.

BACKGROUND OF THE INVENTION

1. Field of the Invention

This invention lies in the field of lipids and the phase transitions of certain lipids from the liquid crystalline phase to the gel phase. In particular, this invention addresses the problem of leakage of internal substances through the membranes of biological cells and liposomes due to passage of these bodies through the phase transition temperature and to prolonged exposure to temperatures below the phase transition temperature.

2. Description of the Prior Art

Various types of biological substances undergo thermotropic phase transitions between a gel phase and a liquid crystalline phase upon cooling down to temperatures close to but not at or below the freezing temperature. Included among such substances are plant and animal cells, bacteria and liposomes. Cooling of these materials to this phase transition region but not to the frozen state is a practical and useful means of preservation for purposes such as storage and shipping, since freezing is destructive of the cell structure and dehydration is impractical in many circumstances.

As they enter and pass through this phase transition, plant cells and liposomes have been observed to undergo leakage of their contents. In cells, this leakage destroys viability and texture, while in liposomes there is a loss in usefulness, particularly when the substance which has leaked out is a functional substance residing in the liposome interior. Liposomes are vesicles formed of ordered phospholipid bilayers encapsulating an aqueous phase. By incorporating functional molecules such as pharmaceuticals, imaging agents, skin care agents and other useful substances as solutes in the encapsulated aqueous phase, researchers have developed liposomes as useful carriers of these substances. Liposome formulations are thus of interest for such industries as the cosmetics industry and the pharmaceuticals industry, and the leakage problem is a potential obstacle to their stability during storage, shipping and handling.

SUMMARY OF THE INVENTION

It has now been discovered that in both liposomes and biological cells, including both plant cells and animal cells, the leakage that occurs upon cooling through the thermotropic phase transition temperature is markedly reduced and in some cases eliminated entirely by treatment of the liposomes or cells with proteins known as antifreeze proteins and antifreeze glycoproteins. It has also been discovered that antifreeze proteins and antifreeze glycoproteins are effective in reducing or eliminating the phase separation that occurs in heterogeneous lipid bilayers, i.e., those whose composition is a mixture of distinct lipids rather than a homogeneous lipid composition. In either case, treatment is readily achieved in a variety of ways, including suspending the liposomes or cells in a liquid solution in which the proteins are dissolved. The whole proteins have been found to be more effective than their component parts, including individual amino acids prominently occurring in the protein structure, poly(amino acid) fragments of the proteins, and glycosylated amino acids included in the protein structure, as well as other naturally occurring proteins and common cryogenic preservation agents. It has also been discovered that certain fractions of antifreeze glycoproteins are surprisingly superior to other fractions. A still further discovery is that when naturally occurring antifreeze proteins are used, the extraction of the antifreeze proteins with an organic solvent prior to their use in treating the liposomes or cells significantly improves the effectiveness of the antifreeze proteins in reducing or eliminating leakage.

This invention thus finds utility in the preservation of animal tissue and of fruits and vegetables and other useful plants, both as food sources and as sources of extracts for pharmaceutical purposes, cosmetic purposes and other therapeutic and generally beneficial purposes, and also in the preservation of liposomes encapsulating beneficial functional substances.

These and other features and advantages of the invention will become apparent from the description which follows.

DETAILED DESCRIPTION OF THE INVENTION AND PREFERRED EMBODIMENTS

Figure 1:
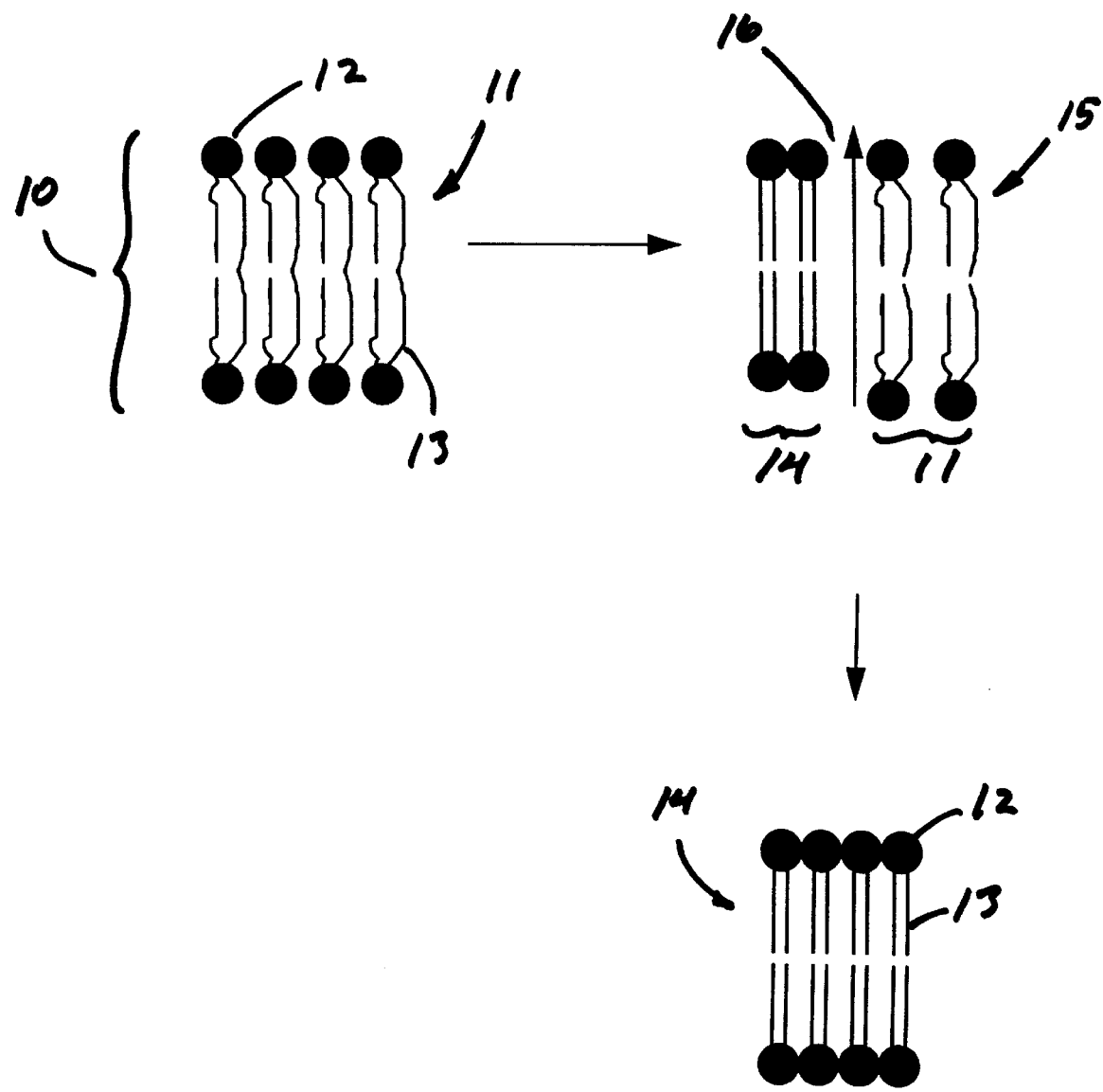
FIG. 1 is a diagram showing the phase transition of a lipid bilayer from the liquid crystalline phase to the gel phase, and passing through the transition phase where leakage across the bilayer occurs due to an increase in permeability arising from packing defects of the lipid molecules.

The thermotropic phase transition is undergone by lipids as they pass between the liquid crystalline (i.e., fluid) and gel (i.e., solid) phases. The cause of the leakage that occurs during this transition is illustrated in FIG. 1, which shows a lipid bilayer 10 undergoing the transition. The lipid molecules in the bilayer, when in liquid crystalline form 11, are loosely aligned according to their hydrophilic 12 and lipophilic 13 regions, the lipophilic regions 13 facing each other, away from the aqueous environment. The loose structure imparts flexibility, but the distance between the loosely aligned molecules is small enough to limit the permeability of the lipid bilayer. After having passed the phase transition temperature, the lipid molecules in solidified (gel) form 14 are scrupulously aligned and more closely packed, further limiting permeability, if not eliminating it entirely. The transitional phase 15, however, is a combination of the loosely packed liquid crystalline phase 11 and the densely packed gel phase 14, and regions where the two phases are in contact contain packing defects 16. The packing defects cause an increase in permeability, greater than that of either the liquid crystalline phase or the gel phase, and hence leakage of large molecules through the bilayer. This is distinct from the ion channels addressed by Rubinsky et al., U.S. Pat. No. 5,358,931. Lipid bilayers do not contain ion channels, and the leakage resulting from defects in the bilayer molecule packing in the transition phase is a distinct phenomenon. This leakage is corrected by the present invention.

Figure 2:
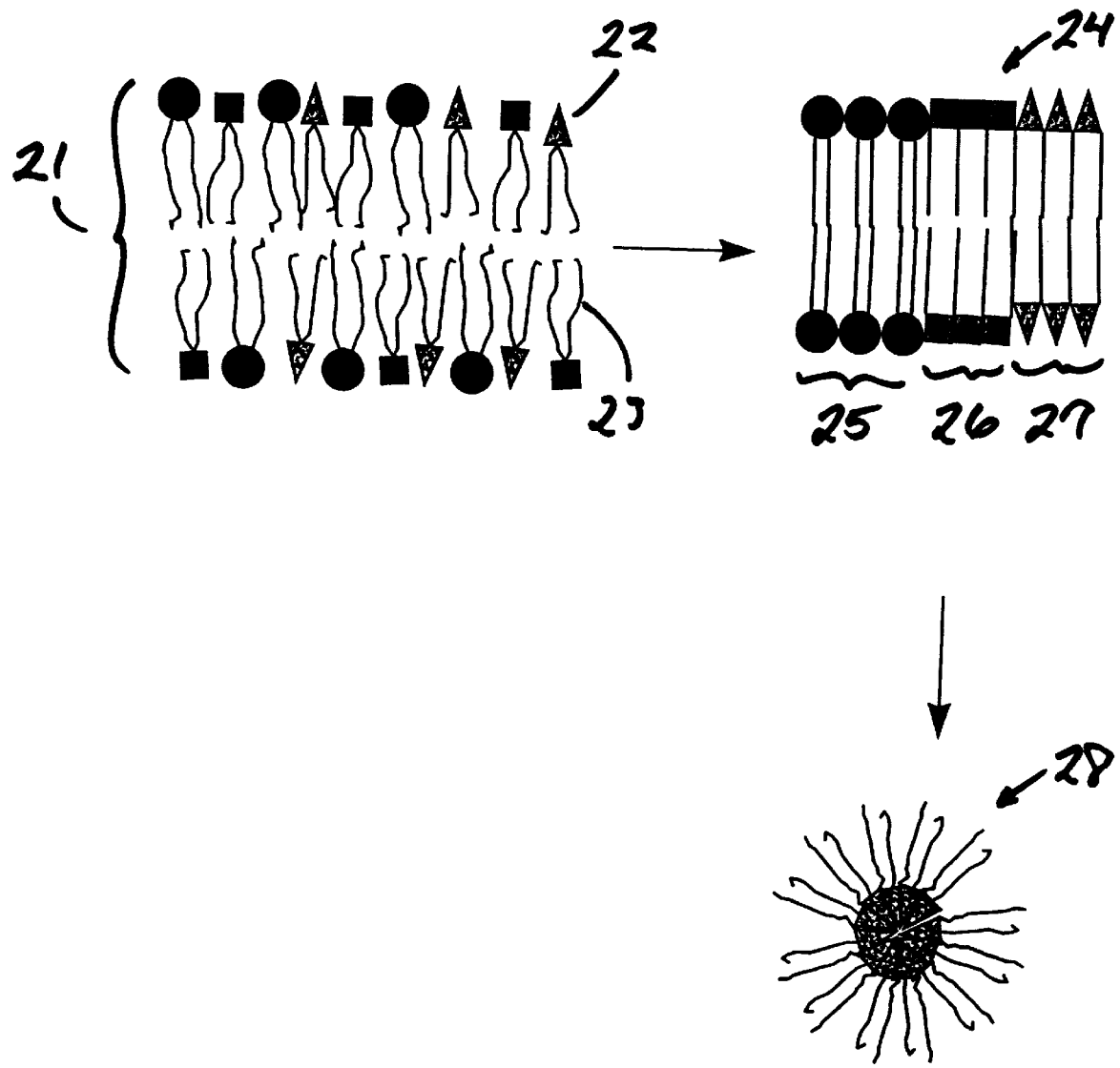
FIG. 2 is a diagram showing the phase separation of a heterogeneous lipid bilayer upon storage in the gel phase.

Lipid bilayers that contain two or more distinct lipids mixed together, generally in a random array, undergo a further transition during storage in the gel phase, this transition being potentially permanent and more damaging. As shown in FIG. 2, the bilayer in liquid crystalline form 21 consists of the lipid molecules loosely aligned according to their hydrophilic 22 and lipophilic 23 regions as in the homogeneous bilayer of FIG. 1. The difference here is that three different lipids are included in each layer of the bilayer, represented by the three different geometrical shapes (circles, squares., triangles) of the hydrophilic regions. Transition into the gel phase 24 finds the lipid molecules in rigid alignment, but separated into pure domains 25, 26, 27, each consisting of molecules of a single lipid. In many cases, this separation into domains, also known as lateral phase separation, is irreversible, i.e., the different lipids upon rewarming do not re-mix. Certain lipids, notably phosphatidylethanolamines, separate completely and form non-bilayer phases 28, which are irreversible as well. This leads to massive leakage across the bilayer and thus to permanent damage. These phase separations are also corrected by the present invention.

The existence of naturally-occurring macromolecular species known as "antifreeze proteins," "thermal hysteresis proteins," "antifreeze glycoproteins," and "antifreeze polypeptides" is well known and widely reported in the literature. The discovery of antifreeze glycoproteins, for example, was first reported by DeVries, A. L., and D. E. Wohlshlag, in "Freezing Resistance in Some Antarctic Fishes," *Science* 163:1073–1075 (7 Mar. 1969). DeVries and Wohlshlag observed that various species of fish surviving in water at temperatures averaging −1.87° C. over the course of a year did so despite having insufficient levels of sodium chloride and other low molecular weight substances in their blood to depress the freezing point by conventional freezing point depression. DeVries and Wohlshlag were able to attribute the survival of these species to the presence of certain glycosylated proteins having molecular weights ranging from about 2,500 to about 34,000, which are now referred to as antifreeze glycoproteins or "AFGPs." Further investigations revealed that many species of north temperate and Arctic fishes carry antifreeze compounds in their blood. Some of these compounds are glycoproteins, while others contain no sugar moieties and are referred to as antifreeze polypeptides or proteins ("AFPs"), with molecular weights ranging from about 3,300 to about 12,000. Furthermore, while the compounds lower the freezing point, the melting point remains unaffected, hence the term "thermal hysteresis proteins."

Antifreeze proteins and glycoproteins have been isolated from a wide variety of sources, and these sources and the structures of the various proteins obtained from them have been reported extensively in the literature. The sources include both fish species and non-fish species, and are listed in Tables I and II below.

TABLE I

THERMAL HYSTERESIS PROTEINS OF FISH SPECIES

| Protein Type, Composition and Size | Source Fish Species | Trivial Name of Fish species |
|---|---|---|
| Antifreeze | Antarctic notothenioids: | |
| glycoproteins (AFGPs): contain alanine, threonine and Gal-GalNAc disaccharide: | *Pagothenia borchgrevinki* *Trematomus borchgrevinki* *Trematomus bernachii* *Dissostichus mawsoni* | Antarctic cod |
| | Northern ocean gadoids: | |
| M.W.: 2,600–33,700 | *Gadus agac* | Greenland cod |
| | *Gadus morhua* | Atlantic cod |
| | *Microgadus tomcod* | Atlantic tomcod |
| | *Boreogadus saida* | Arctic polar cod |
| | *Eligenus gracilis* | Saffron cod |
| Antifreeze | Righteye flounders: | |
| Polypeptides (AFPs), Type I: alanine-rich; M.W.: 3,300–6,000 | *Pseudopleuronectus americanus* | Winter flounder |
| | *Limanda ferruginea* | Yellowtail flounder |
| | Cottids: | |
| | *Myoxycephalus scorpius* | Shorthorn sculpin |
| | *Myoxycephalus aenaeus* | Grubby sculpin |
| | *Myoxycephalus scorpiodes* | Arctin sculpin |
| Antifreeze | Cottid: | |
| Polypeptides (AFPs), Type II: cysteine-rich; homologous to C-type lectins; M.W.: 14,000–16,000 | *Hemitripterus americanus* | Sea raven |
| | *Osmerus mordex* | Smelt |
| | *Clupea harengus harengus* | Herring |

TABLE I-continued

THERMAL HYSTERESIS PROTEINS OF FISH SPECIES

| Protein Type, Composition and Size | Source Fish Species | Trivial Name of Fish species |
|---|---|---|
| Antifreeze | Eel pouts: | |
| Polypeptides (AFPs), Type III: no cysteines, and not rich in alanines; M.W.: 5,000–6,700 | *Macrozoarces americanus* *Rhigophila dearborni* *Lycodes polaris* | Ocean pout Antarctic eel pout Arctic eel pout |

TABLE II

NON-FISH SOURCES OF THERMAL HYSTERESIS PROTEINS

A. Insects Other Than Beetles:

| Order | Species |
|---|---|
| Collembola | 7 spp. |
| Plecoptera | *Arcynopteryx compacta* |
| Orthoptera | *Parcoblata pennsylvanica* |
| Hemiptera | *Oncopeltus fasciatus* |
| Mecoptera | *Boreus westwoodi* |
| Lepidoptera | *Choristoneura fumiferana* |

B. Coleoptera (Beetles):

| Family | Species |
|---|---|
| Tenebrionidae | *Tenebrio molitor* |
| | *Meracantha contracta* |
| | *Uloma impressa* |
| | *Platydema sp.* |
| Elateridae | *Ampedus lineatus* |
| | *Ampedus sp.* |
| | *Lepidotus discoideus* |
| | *Melanotus sp.* |
| Cucujidae | *Cucujus clavipes* |
| Pyrochridae | *Dendroides canadensis* |
| Lampyridae | *Photinus sp.* |
| Coccinellidae | *Coccinella novemnotata* |
| Scolytidae | *Ips acuminatus* |
| Cerambycidae | *Rhagium inquisitor* |

C. Non-Insect Arthropods:

| Animal | Species |
|---|---|
| Spiders | *Philodromus sp.* |
| | *Clubiona sp.* |
| | *Bolyphantes index* |
| Centipede | *Lithobius forficatus* |
| Mite | *Alaskozetes antarcticus* |

D. Other Invertebrates:

| | |
|---|---|
| Mussel | *Mytilus edulis* |

The proteins which have been the most extensively studied, and which are the preferred proteins for use in the practice of the present invention, are those isolated from fish species. As indicated in Table I, these proteins include both glycosylated proteins (AFGPs) and non-glycosylated proteins (AFPs), and the latter fall within three general categories, designated Type I, Type II, and Type III.

The AFGPs generally consist of a series of repeats of the tripeptide unit alanyl-alanyl-threonyl, with the disaccharide β-D-galactosyl-(1→3)-α-N-acetyl-D-galactosamine attached to the hydroxyl group of the threonine residue, although variations exist. For example, AFGPs of relatively low molecular weight contain proline and arginine residues in place of some of the alanine and threonine residues, respectively. Chromatographic studies of the AFGPs from representative fish species have revealed eight major molecular weight fractions, as indicated in Table III.

TABLE III

Molecular Weight Fractions of AFGPs From *Pagothenia borchgrevinki*

| Fraction No. | Molecular Weight |
|---|---|
| 1 | 33,700 |
| 2 | 28,800 |
| 3 | 21,500 |
| 4 | 17,000 |
| 5 | 10,500 |
| 6 | 7,900 |
| 7 | 3,500 |
| 8 | 2,600 |

Preferred AFGPs for purposes of the present invention are those of Fraction No. 8, but all fractions are effective.

The AFPs differ from one another to a larger degree than do the AFGPs. As indicated in Table I, the three types of AFPs differ from each other in their residue content. Type I AFPs are rich in alanine residues (about 65%), with most of the remainder consisting of polar residues such as aspartic acid, glutamic acid, lysine, serine and threonine. The molecular weight ranges from about 3,300 to about 6,000. Type II AFPs are considered to be rich in cysteine (actually half-cysteine) residues, and are homologous to C-type lectins. Type II AFPs from the sea raven contain 7.6% cysteine, 14.4% alanine, 19% total of aspartic and glutamic acids, and 8% threonine. The molecular weight ranges from about 14,000 to about 16,000. Type III AFPs are devoid of cysteine residues and not rich in alanine residues. No conspicuous dominance of any particular amino acid is evident, and the amino acid content is evenly divided between polar and non-polar residues. The molecular weight ranges from about 5,000 to about 6,700. All percents referred to in this paragraph are on a mole basis.

Antifreeze proteins from insects are primarily AFPs of Type II, and typical compositions in terms of amino acid residues are those of the *Choristoneura fumiferana* (spruce budworm) and *Tenebrio molitor* (beetle). These are listed in Table IV, which also includes the amino acid composition of the sea raven for comparison.

TABLE IV

Comparative Amino Acid Compositions of Type II AFPs

| Amino Acid Residue | Spruce Budworm Fraction II | Beetle | Sea Raven |
|---|---|---|---|
| Asx | 9.5 | 5.3 | 10.7 |
| Thr | 6.0 | 2.3 | 7.9 |
| Ser | 13.0 | 11.1 | 8.2 |
| Pro | 5.0 | 0.0 | 6.7 |
| Glx | 11.0 | 12.4 | 9.1 |
| Gly | 15.0 | 11.4 | 8.1 |
| Ala | 8.0 | 5.0 | 14.4 |
| ½-Cys | 6.0 | 28.0 | 7.6 |
| Val | 3.0 | 2.3 | 1.2 |
| Met | 0.0 | 0.0 | 5.4 |
| Ile | 1.2 | 1.0 | 1.7 |
| Leu | 6.5 | 2.2 | 6.2 |
| Tyr | 1.0 | 0.0 | 1.2 |
| Phe | 2.2 | 0.0 | 2.0 |
| Lys | 3.1 | 15.4 | 2.1 |
| His | 0.0 | 3.1 | 2.5 |
| Trp | 0.0 | 0.0 | 2.8 |
| Arg | 8.0 | 0.0 | 2.3 |

Antifreeze proteins and glycoproteins can be extracted from the sera or other bodily fluids of fish or insects by conventional means. Isolation and purification of the proteins is readily achievable by chromatographic means, as well as by absorption, precipitation, and evaporation. Other methods, many of which are described in the literature, will be readily apparent to those skilled in the art.

Extraction of the antifreeze proteins can be performed with any organic solvent that has limited or no miscibility with water and thus can be phase separated from aqueous solutions of the proteins. Such organic solvents include aldehydes, ketones, esters, alcohols, ethers, thiols, thioesters, thioethers, aliphatics (paraffins, olefins and acetylenes), alicyclics, aromatics, and heterocyclics. Specific examples will be readily apparent to those skilled in the art. Solvents of particular interest are ketones and ethers, examples of which are acetone, methyl ethyl ketone, methyl isobutyl ketone, diethyl ether, dipropyl ether, dibutyl ether, and butyl ethyl ether. Particularly preferred are acetone and diethyl ether.

Thermal hysteresis proteins can also be produced synthetically, either by conventional chemical synthesis methods or by methods involving recombinant DNA. The DNA coding sequences of the genes which form these proteins have been elucidated and are extensively reported. See, for example, DeVries, A. L., et al., *J. Biol. Chem.* 246:305 (1971); Lin, Y., et al., *Biochem. Biophys. Res. Commun.* 46:87 (1972); Yang, D. S. C., et al., *Nature* 333:232 (1988); Lin, Y., *Proc. Natl. Acad. Sci. U.S.A.* 78:2825 (1981); Davies, P. L., et al., *J. Biol. Chem.* 79:335 (1982); Gourlie, B., et al., *J. Biol. Chem.* 259:14960 (1984); Scott, G. K., et al., *Can. J. Fish. Aquat. Sci.* 43:1028 (1986); Scott, G. K., et al., *J. Mol. Evol.* 27:29 (1988). Successful microinjection of the AFP gene into species other than its native species has also been reported. See, for example, Zhu, Z., et al., *Angew. Ichthyol.* 1:31 (1985); Chourrout, D., et al., *Aquaculture* 51:143 (1986); Dumman, R. A., et al., *Trans. Am. Fish. Soc.* 116:87 (1987); Fletcher, G. L., et al., *Can. J. Fish Aquat. Sci.* 45:352 (1988); Maclean, N. D., et al., *Bio Technology* 5:257 (1987); Stuart, G. W., et al., *Development* 103:403 (1988); McEvoy, T., et al., *Aquaculture* 68:27 (1988); Ozato, K, et al., *Cell Differ.* 19:237 (1986).

As indicated above, one of the fields of application of the present invention is the use of antifreeze proteins and glycoproteins in the treatment of liposomes. Liposomes are formed from standard vesicle-forming lipids, which generally include neutral and negatively charged phospholipids and a sterol, such as cholesterol. The choice of a particular lipid is generally based on such factors as the desired size and stability of the resulting liposomes in the bloodstream or other intended mode of administration. The effect here claimed is independent of lipid composition, however.

A commonly used lipid component in the liposomes is phosphatidylcholine. Phosphatidylcholines to which a variety of acyl chain groups of varying chain length and degree of saturation have been bonded are commercially available or may be isolated or synthesized by well-known techniques. The more common phosphatidylcholines are those containing saturated fatty acids with carbon chain lengths in the range of $C_{14}$ to $C_{22}$, although phosphatidylcholines formed from mono- or diunsaturated fatty acids and from mixtures of saturated and unsaturated fatty acids are of use as well. This invention also extends to liposomes formed from phosphonolipids in which the fatty acids are linked to glycerol via ether linkages rather than ester linkages; liposomes formed from sphingomyelin or phospholipids with head groups other than choline, such as ethanolamine, serine, glycerol and inositol; and liposomes formed from cholesterol, diglycerides, ceramides, phosphatidylethanolamine-polyoxyethylene conjugates and phosphatidic acid-polyoxyethylene conjugates. When a sterol such as cholesterol is present, the mole ratio of sterol to phospholipid is generally from about 0.1 to 1.0. Examples of liposome compositions are distearoylphosphatidylcholine/cholesterol, dipalmitoylphosphatidylcholine/cholesterol, and sphingomyelin/cholesterol.

Liposomes may be prepared by a variety of methods described in the literature. Descriptions appear for example in Szoka, et al., *Ann. Rev. Biophys. Bioeng.* 9:467 (1980); U.S. Pat. Nos. 4,235,871, 4,501,728, and 4,837,028; the text *Liposomes*, Marc J. Ostro, ed., Marcel Dekker, Inc., New York, 1983, Chapter 1; and Hope, et al., *Chem. Phys. Lip.* 40:89 (1986), all of which are incorporated herein by reference. One method involves dissolving the vesicle-forming lipids in a suitable organic solvent or solvent system and drying the solution under vacuum or an inert gas to form a thin lipid film. The liposomes produced by this method are multilamellar vesicles which are heterogeneous in size. To achieve a more homogeneous lipid mixture, the film can be redissolved in a suitable solvent such as t-butanol, then lyophilized, covered with an aqueous buffered solution and allowed to hydrate.

Liposomes can be sized by a variety of known techniques. One method is sonication, specifically bath or probe sonication, resulting in a progressive size reduction. Another method is homogenization by the use of shearing energy to fragment large liposomes into smaller ones. A third method is the extrusion of liposomes through a small-pore polycarbonate membrane or an asymmetric ceramic membrane.

Functional compounds such as drugs, cosmetics, imaging agents, and the wide variety of other materials supplying biological utility of some kind can be incorporated into the liposome interior by conventional means. The most common such means are encapsulation and transmembrane potential loading.

Encapsulation of a drug or other functional agent can be achieved by dissolving the agent and the liposome components in an organic solvent in which all species are miscible, then concentrating the resulting solution and evaporating the solvent to a dry film. A buffer is then added to the film and liposomes are formed with the agent incorporated into the vesicle walls. Alternatively, the agent can be dissolved in a buffer and added to a dry film formed solely from the lipid components. The buffer can be any biologically compatible buffer solution. Examples are isotonic saline, phosphate buffered saline, and other low ionic strength buffers. The buffer method will result in liposomes with the agent encapsulated in the aqueous interior of the liposome. In either method, the agent will constitute from about 0.01 ng/mL to about 50 mg/mL of the liposome suspension. The liposomes with the agent incorporated in the aqueous interior or in the membrane are then optionally sized as described above.

Transmembrane potential loading has been described in detail in U.S. Pat. No. 4,885,172, U.S. Pat. No. 5,059,421, and U.S. Pat. No. 5,171,578, the contents of which are incorporated herein by reference. The method can be used to load any conventional drug which can exist in a charged state when dissolved in an appropriate aqueous medium. The potential is established across the bilayers of the liposomes by producing liposomes having different internal and external media such that a concentration gradient of one or more charged species (such as $Na^+$, $K^+$ and/or $H^+$) is imposed across the bilayers. To load a drug which in ionized form is negatively charged, for example, a liposome created with an inside potential which is positive relative to the outside potential is used.

Biological cells to which this invention is applicable include a wide range of living cells that undergo thermotropic phase transitions. This includes both animal cells and plant cells. Among animal cells, mammalian cells are of particular interest, as well as mammalian tissues, organs and organisms. Examples of mammalian cells to which the invention is applicable are mammalian oocytes, hepatocytes, erythrocytes and leukocytes. Examples of tissues and organs are tissue of livers, hearts, and kidneys, and the organs themselves. Examples of organisms are embryos, and self-sustaining whole animals.

Plant cells to which the present invention is applicable include cells from a wide variety of plants. The cells which will benefit from the invention are those which undergo a thermotropic phase transition in temperature regions above the freezing point. The phenomenon observed in these plant materials is cold shock, or loss through the membrane of low molecular weight constituents. These plant materials include fruits, vegetables, grains, and other food-source plants, and the type and form of cells which exhibit this behavior range from seeds to germinated seedlings to mature plants, including portions of plants such as leaves, fruits, vegetables, stalks and roots.

The use of this invention to reduce or eliminate phase separations in lipid bilayers is applicable to any bilayers made up of two or more molecularly distinct lipids that have a tendency to undergo phase separation upon the crystallization that occurs in the gel phase. The term "molecularly distinct" is used herein to denote species that differ in molecular structure while still being lipids, i.e., having both hydrophilic and lipophilic portions in a single molecule. Thus, dipalmitoylphosphatidylcholine, egg phosphatidylethanolamine, dielaidoylphosphatidylcholine, and dimyristoylphosphatidylcholine are all lipids but all molecularly distinct from each other. The term "phase separation" is used herein to include both lateral phase separation within a single bilayer and total segregation into separate structures. In lateral phase separation, the bilayer and its components remain intact although the molecularly distinct lipid components of the bilayer rearrange into single-component clusters or domains within the bilayer. In total segregation, the bilayer breaks up into single-component structures containing only one molecularly distinct lipid, in some cases forming non-bilayer structures such as those shown in FIG. 2. The term "separation-reducing amount" is used herein to denote an amount of thermal hysteresis protein that reduces the degree to which either type of separation occurs, to a degree that will preserve the utility of the biological structure.

The cells, tissues or liposomes can be treated with the antifreeze proteins and glycoproteins in accordance with this invention in a variety of ways. A convenient method is the incubation of the cells or liposomes as a suspension in an aqueous solution of the treatment agent. For suspensions in which the cells or liposomes constitute from about 0.1 mg/mL to about 1 mg/mL of the suspension, the antifreeze proteins or glycoproteins will be present in an amount preferably ranging from about 0.3 mg/mL to about 30 mg/mL of the suspension, more preferably from about 1 mg/mL to about 20 mg/mL, and most preferably from about 3 mg/mL to about 10 mg/mL. The incubation will be performed at a temperature above the phase transition temperature, and the cells or liposomes can be maintained in the suspension until ready for use or concentrated or recovered from the suspension, provided that they are maintained in an environment which will prevent outward diffusion of the antifreeze proteins or glycoproteins. Other means of contacting the cells or liposomes with antifreeze proteins or glycoproteins will be readily apparent to those skilled in the handling of cells, tissues or liposomes.

The following examples are offered by way of illustration rather than limitation.

EXAMPLE 1

This example illustrates the effect of antifreeze glycoproteins and antifreeze proteins in inhibiting leakage from dielaidoylphosphatidylcholine liposomes during a phase transition.

Liposomes were prepared from dielaidoylphosphatidylcholine (DEPC) vesicles in a conventional manner, except that carboxyfluorescein was included in the forming solution at a concentration of 200 mM and accordingly trapped inside the resulting liposomes as a marker. Once formed, liposomes were sized by extrusion through polycarbonate filters, using the commercial apparatus produced by Avestin, Inc., Ottawa, Ontario, Canada. Excess carboxyfluorescein not trapped by the liposomes was removed by passing the liposomes through a Sephadex column. The resulting liposome suspensions had a liposome concentration of 20 mg/mL.

Antifreeze glycoproteins obtained from *Trematomus borchgrevinki*, including combined chromatographic fractions 1–8 as well as subcombinations including fractions 2–6, 5–7 and 3–4 were used. In additional experiments, antifreeze proteins (Type I) obtained from *Pseudopleuronectus americanus* were used. The AFPs and AFGPs were tested against a control of untreated liposomes, and comparisons were also made against other potential treatment agents. These included alanine, galactose, N-acetyl galactosamine, glycerol, proline, Rock Fish blood serum and ovotransferrin. Alanine, galactose and N-acetyl galactosamine were included because they are prominent components of AFPGS.

For each experiment in which the liposomes were treated with antifreeze proteins, antifreeze glycoproteins, or any of the comparative substances, the treatment agent was added to the aqueous liposome suspension to achieve a range of final concentrations as shown below. To achieve the phase transition, the liposomes, both treated and control, were placed in a fluorometer and cooled from 20° C. to 0° C. in a temperature controlled cuvette at a rate of 0.5° C./minute. Leakage was assayed by the increase in fluorescence observed continuously as carboxyfluorescein leaked into the external medium.

The results are listed in Table V below, where the experiments are arranged in increasing order of percent leakage.

TABLE V

Percent Leakage of Carboxyfluorescein From Dielaidoylphosphatidylcholine Vesicles During Cooling Through Phase Transition With Various Treatment Agents

| Treatment Agent | Concentration | Percent Leakage |
|---|---|---|
| AFGP 1–8* | 4 mg/mL | 3 |
| AFGP 1–8 | 1 mg/mL | 5 |
| AFGP 2–6 | 1 mg/mL | 9 |
| AFGP 5–7 | 1 mg/mL | 10 |
| AFGP 8 | 4 mg/mL | 21 |
| AFP Type I | 1 mg/mL | 23 |

TABLE V-continued

Percent Leakage of Carboxyfluorescein From
Dielaidoylphosphatidylcholine Vesicles During Cooling
Through Phase Transition With Various Treatment Agents

| Treatment Agent | Concentration | Percent Leakage |
| --- | --- | --- |
| AFGP 3–4 | 1 mg/mL | 33 |
| AFGP 8 | 1 mg/mL | 35 |
| none (control) | | 55 |
| glycerol | 0.4M | 58 |
| N-acetyl galactosamine | 1 mg/mL | 59 |
| proline | 1 mg/mL | 62 |
| Rock Fish blood serum | 2 mg/mL | 70 |
| ovotransferrin | 1 mg/mL | 81 |

*For AFGP entries, the number following "AFGP" indicates the AFGP fraction(s).

Figure 3:
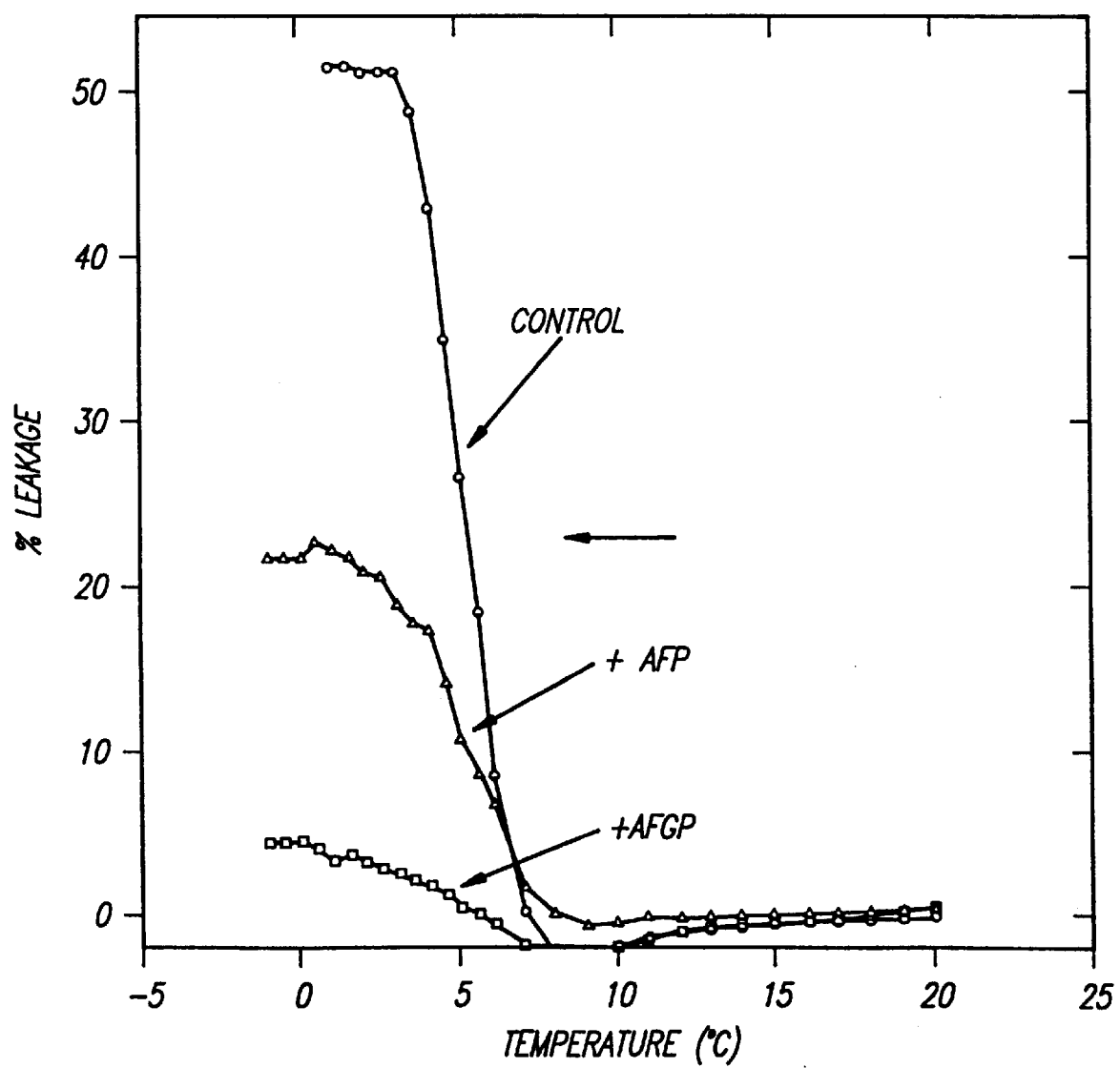
FIG. 3 is a plot showing the leakage of a marker compound from liposomes as temperature is lowered through the thermotropic transition temperature. Liposomes treated in accordance with the invention are compared with untreated liposomes.

These tests show that the intact AFGPs have a significant effect in reducing leakage associated with the phase transition, and are consistently more effective than both the AFGP components and fractions and the control. Some of the treatment agents are in fact shown to increase the leakage rather than reduce it. Leakage curves are shown in FIG. 3, where the open squares (□) represent 1 mg/mL AFGP 1–8, the open triangles (Δ) represent 1 mg/mL AFP (Type I), and the open circles (○) represent the control. The progression in each curve is from right to left as the temperature is lowered through the phase transition temperature of approximately 5° C.

EXAMPLE 2

This example presents further test results on carboxyfluorescein-marked DEPC liposomes, with emphasis on the differences between AFGP fractions, constituent subunits of AFGPs and denatured AFGPs.

The procedures of Example 1 were followed, with bovine serum albumin (BSA) and fractions 6, 7 and 8 of the AFGPs denatured at 80° C. for 30 minutes as additional comparative treatment agents. The results are listed in Table VI below.

TABLE VI

Percent Leakage of Carboxyfluorescein From
Dielaidoylphosphatidylcholine Vesicles During Cooling
Through Phase Transition With Various Treatment Agents

| Treatment Agent | Concentration | Percent Leakage |
| --- | --- | --- |
| AFGP 8* | 10 mg/mL | 0 |
| AFGP 8 | 1 mg/mL | 15 |
| AFGP 2–6 | 1 mg/mL | 5 |
| AFGP 5–7 | 2 mg/mL | 9 |
| AFGP 1–5 | 1 mg/mL | 20 |
| AFGP 6 | 1 mg/mL | 40 |
| alanine | 1 mg/mL | 42 |
| galactose | 1 mg/mL | 45 |
| BSA | 1 mg/mL | 47 |
| none (control) | | 50 |
| denatured AFGP 6–8 | 1 mg/mL | 55 |
| N-acetyl galactosamine | 1 mg/mL | 59 |
| proline | 1 mg/mL | 62 |
| Rock Fish blood serum | 2 mg/mL | 70 |

*For AFGP entries, the number following "AFGP" indicates the AFGP fraction(s).

These data show that at high concentrations, Fraction 8 leads to complete inhibition of leakage. At a much lower concentration, Fractions 2 through 6 inhibit leakage by as much as 95%. In addition, these data confirm the findings of Example 1, that the components of the AFGPs (alanine, galactose and N-acetyl galactosamine) are not effective, and that heat denaturing destroys the effectiveness of the protein.

Figure 4:
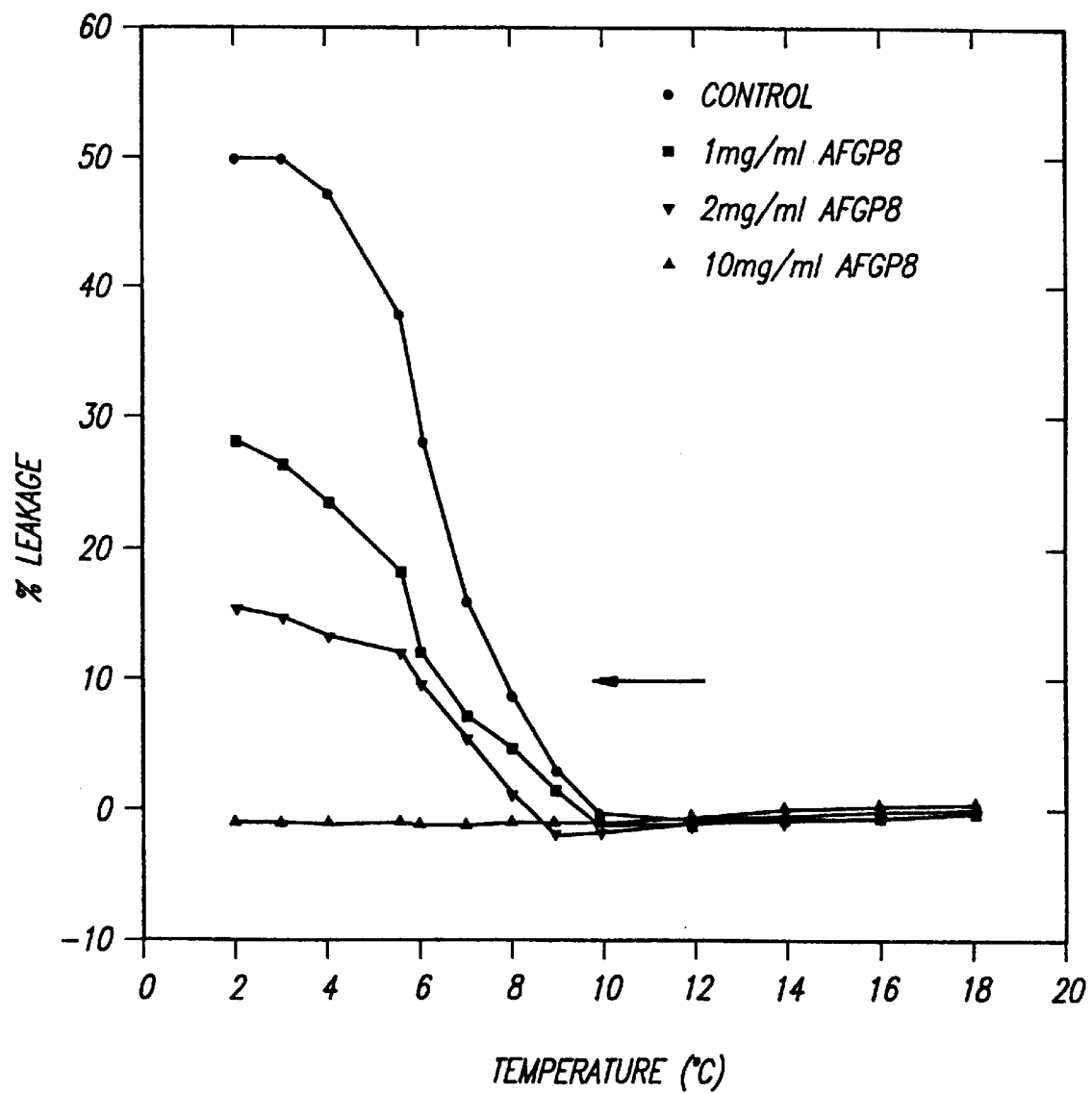
FIG. 4 is a plot similar to that of FIG. 3, but additionally showing the effect of varying the amount of treatment agent used in the treatment of the liposomes.

The effect of increasing the concentration of AFGP Fraction 8 is shown in FIG. 4. Once again, the progression in each curve is from right to left as the temperature is lowered through the phase transition temperature of approximately 22° C. The circles (●) represent the control with no treatment agent used; squares (■) represent the sample treated with 1 mg/mL AFGP 8; inverted triangles (▼) represent the sample treated with 2 mg/mL; and triangles (▲) represent the sample treated with 10 mg/mL.

Figure 5:
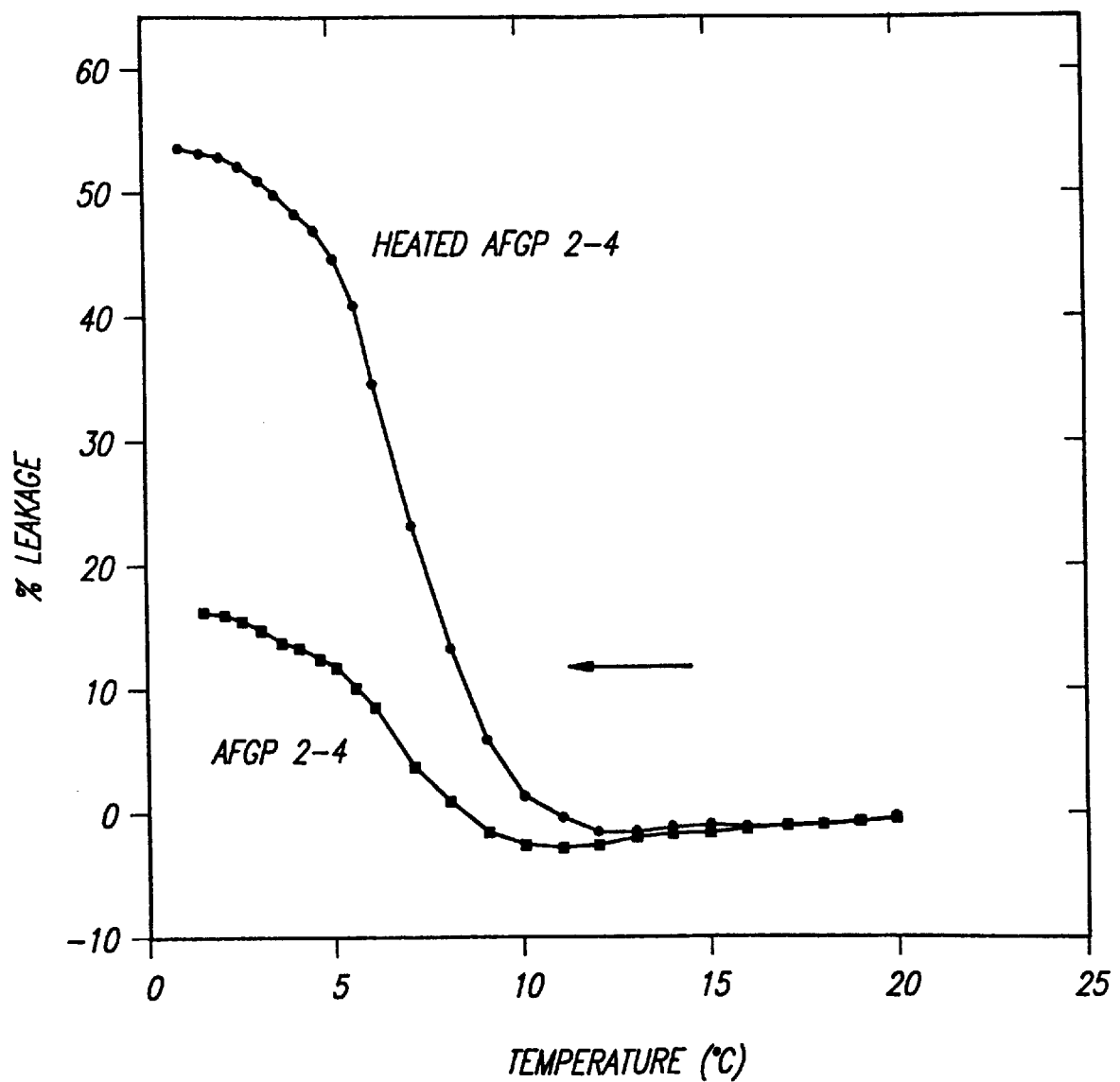
FIG. 5 is a plot similar to that of FIG. 3, but additionally showing the effect of using a heat-denatured treatment agent in comparison to one which had not been denatured.

The effect of heat denaturation is shown in FIG. 5. The AFGP fractions used in the data shown in this Figure are Fractions 2–4 combined. The circles represent these fractions used after heat denaturation at 80° C. for thirty minutes, while the squares represent the same fractions used without heat denaturation.

Figure 6:
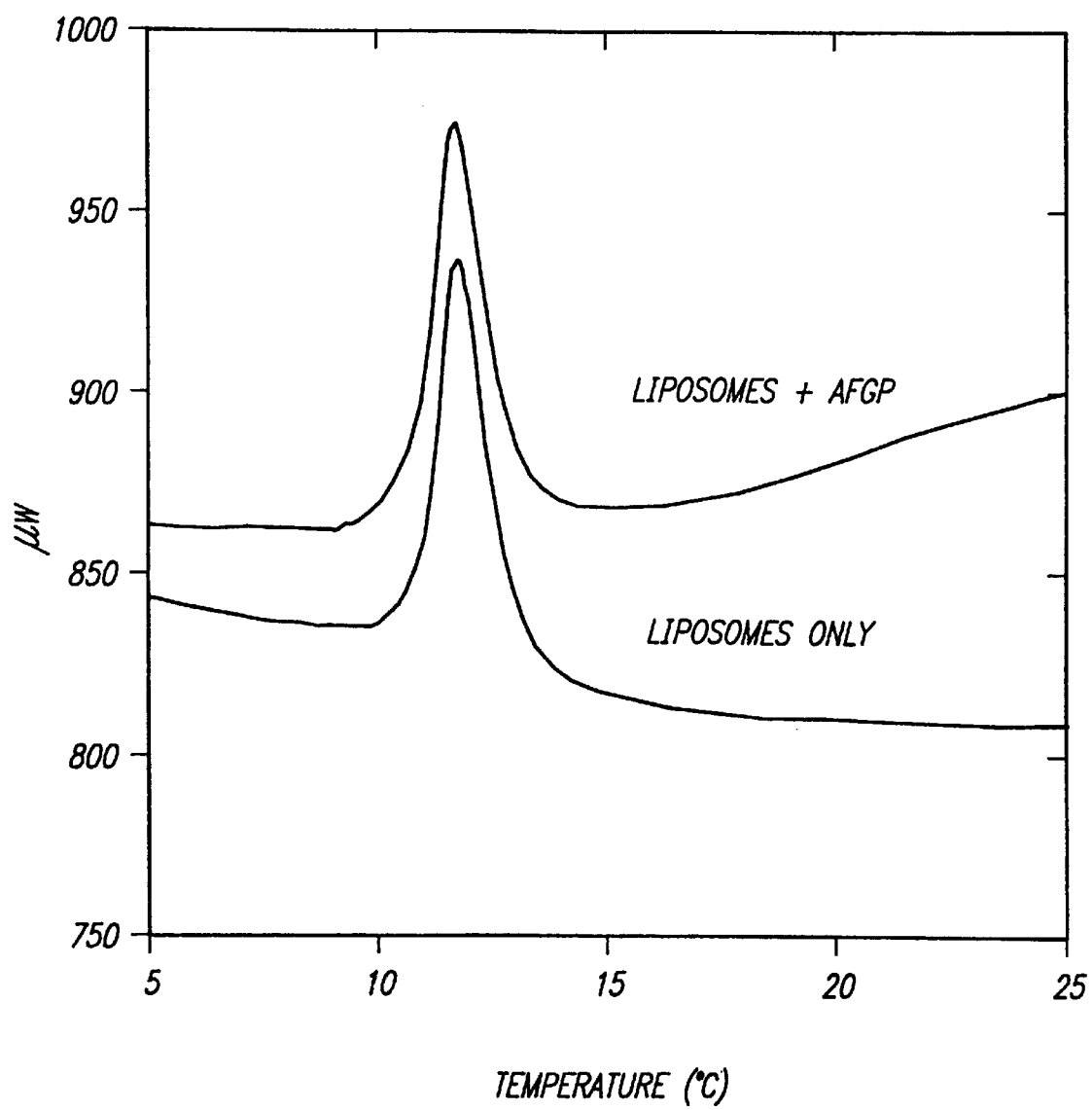
FIG. 6 shows two calorimetric scans, one taken of dielaidoylphosphatidylcholine (DEPC) liposomes treated in accordance with the invention and the other of the same liposomes but untreated.

FIG. 6 is a calorimetric scan of the liposomes whose test data appears in Table II and in FIGS. 4 and 5. Two scans are shown, the upper scan performed on liposomes treated with AFGP fractions 2–6 from Dissostichus mawsoni and the lower scan on liposomes not treated with any treatment agent. The peak seen at approximately 12° C. is a melting endotherm which occurs as the hydrocarbon chains melt. The fact that the peak is present in both scans and occurs at the same location leads to the conclusion that the AFGPs do not achieve their leakage inhibition effect by any effect on the phase transition of the liposomes.

EXAMPLE 3

This example illustrates the leakage occurring during a liposome phase transition in the opposite direction, i.e., with an increase in temperature, and the lack of effect of antifreeze glycoproteins on the leakage.

Figure 7:
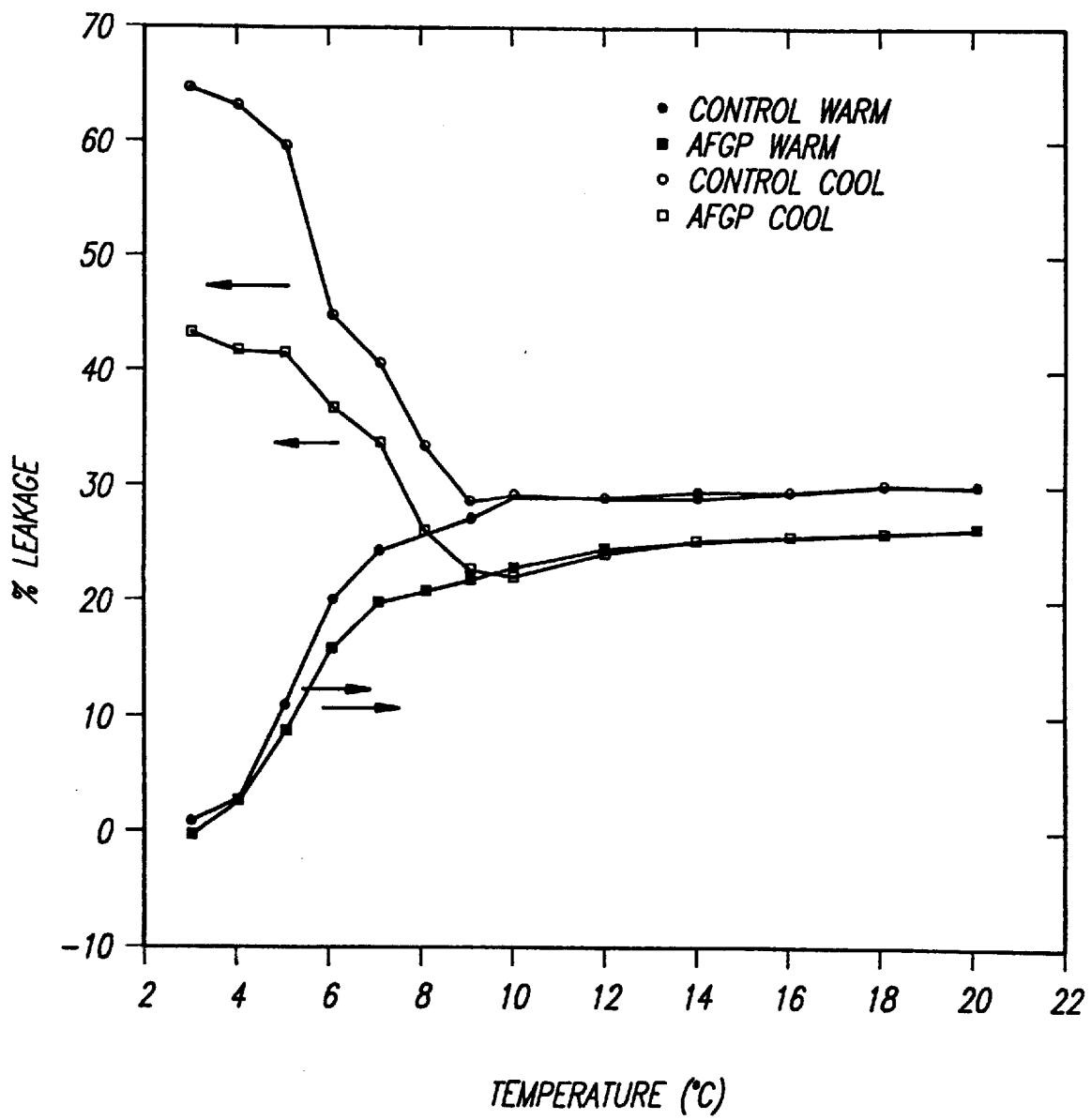
FIG. 7 is a plot showing the leakage of a marker compound from DEPC liposomes, through both a warming past the thermotropic transition temperature and a cooling back to the initial low temperature.

DEPC liposomes were again used in this study. These liposomes were prepared at approximately 23° C., which is above their phase transition temperature. The liposomes were then cooled rapidly through the phase transition. AFGPs Fractions 5–7 from Trematomus bernachii were then added at a concentration of 1 mg/mL. The liposomes were incubated at 4° C. for one hour, and then rewarmed to approximately 21° C. at a rate of 0.5° C./min. The percent leakage was recorded at two-degree intervals by fluorometer. A parallel test was performed on control liposomes which had not been treated with the AFGPs. During the low-temperature incubation, leakage was minimal, but during the slow rewarming, leakage occurred at a rate indistinguishable from the controls. The liposomes were then recooled slowly through the phase transition temperature. The results are shown in FIG. 7, where the filled circles (●) represent the control data taken in the warming direction; the filled squares (■) represent the test data (AFGP-treated vesicles) taken in the warming direction; the open circles (○) represent the control data taken in the cooling direction; and the open squares (□) represent the test data taken in the cooling direction. The plot indicates that the AFGPs inhibit leakage during both cooling and warming. It is possible to achieve this effect by adding the AFGPs either above or below the phase transition.

EXAMPLE 4

This example presents a study of dimyristoylphosphatidylcholine (DMPC) liposomes, showing the phase transitions occurring during warming, and comparing the results obtained with and without antifreeze proteins present.

Liposomes were prepared from DMPC at about 4° C. in a conventional manner, with carboxyfluorescein as a marker, following the procedure described in Example 1. The antifreeze proteins used for treatment were AFGPs Fractions 2–6 from *Dissostichus mawsoni*, added to the liposomes at a concentration of 1 mg/mL while the liposomes were still at the low temperature. Once formed, the vesicles were warmed to 28° C. at a rate of 0.5° C./min while the percent leakage was recorded at one- or two-degree intervals by fluorometer. This was followed by cooling the vesicles back down to 3° C., again at 0.5° C./min while leakage measurements were recorded by fluorometer. The results are shown in FIG. 8, where the circles represent the control liposomes and the squares the AFGP-treated liposomes.

Figure 8:
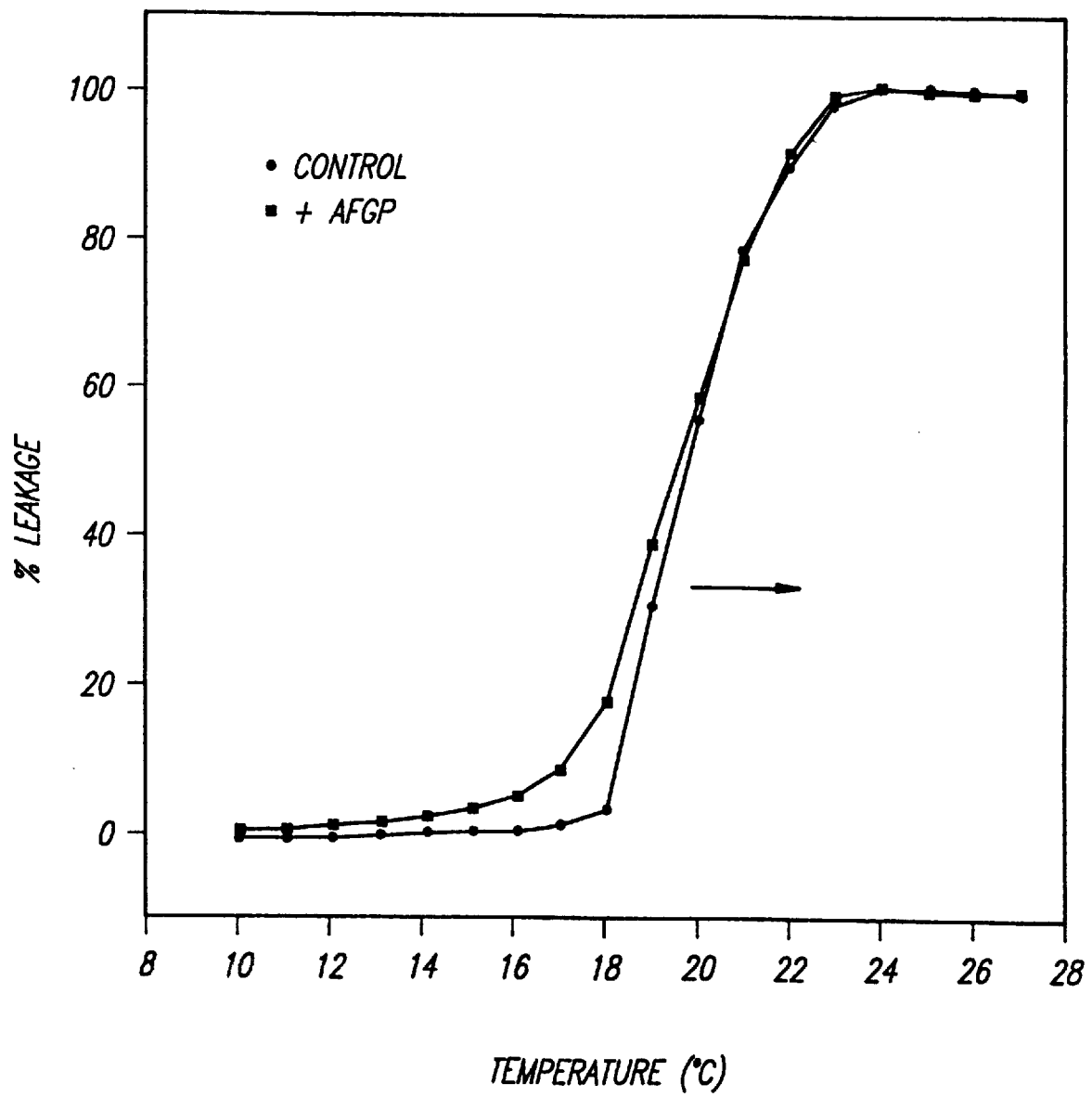
FIG. 8 is a plot showing the leakage of the marker compound from dimyristoylphosphatidylcholine (DMPC) liposomes as the temperature is raised, rather than lowered, through the thermotropic transition temperature.

The data in FIG. 8 show that the AFGPs had essentially no effect on leakage during the phase transition in the direction of increasing temperature.

EXAMPLE 5

This example presents a study of the use of antifreeze proteins after having been extracted with organic solvents to improve the ability of the proteins to protect liposome bilayers during chilling through the phase transition of the liposomes.

One organic solvent used in these experiments was diethyl ether. A solution was prepared by dissolving 10 mg of AFGP Fraction 8 from *Dissostichus mawsoni* in 1 mL of water. Ether (3 mL) was slowly added and the vessel was shaken. The aqueous and ether phases were then allowed to phase separate. Most of the ether fraction was removed with a pipette, and the remainder was evaporated under a stream of nitrogen. The aqueous phase was freeze-dried, yielding the dry, extracted antifreeze protein.

Another organic solvent used was acetone. The same AFGP fraction (10 mg) was dissolved in water, and acetone (3 mL) was added. The vessel was shaken, then cooled to precipitate the protein, spun at 3,500 rpm to pellet the precipitate, and the supernatant over the protein was removed with a pipette, and the residual acetone evaporated under nitrogen. The protein pellet was freeze-dried.

Figure 9:
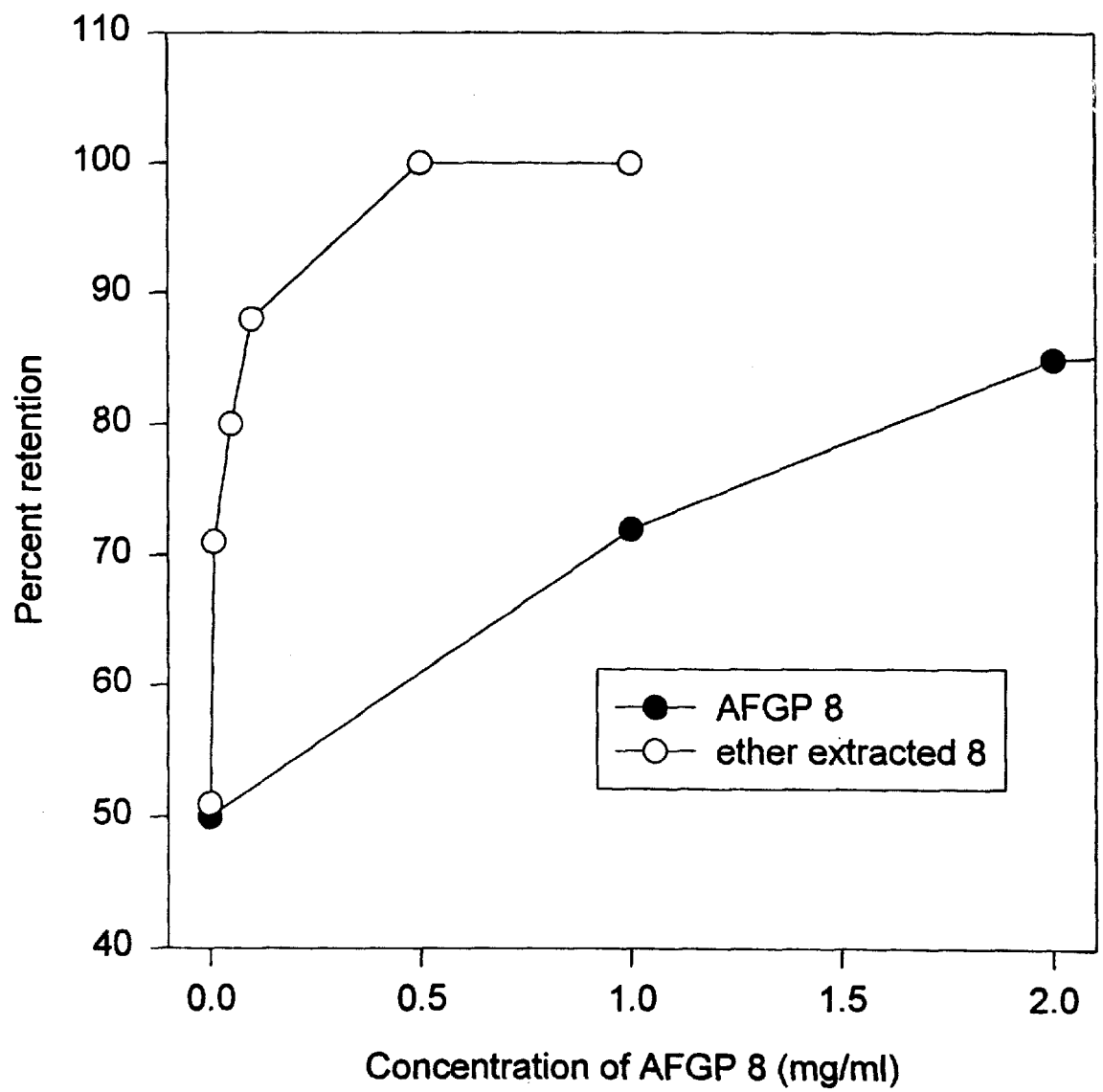
FIG. 9 is a plot of the percent retention of the same marker compound, comparing the use of the treatment agent that had been extracted with ether with unextracted treatment agent.

Liposomes composed of DEPC containing carboxyfluorescein as the marker, as prepared in Example 1, were used. Using different concentrations of AFGP Fraction 8, both extracted and non-extracted, the liposomes were suspended in aqueous solutions of the protein. Cooling was performed and leakage was assayed as in Example 1. The results are shown in FIG. 9, where the filled circles (●) represent data taken with non-extracted AFGP and the open circles (○) represent data taken with AFGP extracted with ether. A significant effect of the protein is seen at concentrations as low as 0.1 mg/mL when using extracted AFGP, and only 0.5 mg/mL was needed to achieve maximal retention of the marker. By contrast, 10 mg/mL of the native protein (non-extracted AFGP) was needed to achieve maximal retention of the marker.

Similar results were obtained with AFGP fractions 2–6, 5–7, 1–5, and 6, and with antifreeze proteins (Type I) obtained from *Pseudopleuronectus americanus*.

EXAMPLE 6

This example illustrates lateral phase separation in a mixture of dipalmitoylphosphatidylcholine (DPPC) and egg phosphatidylethanolamine (egg PE).

Liposomes were prepared from a 1:1 (weight basis) mixture of DPPC and egg PE, and from each of these lipids alone. For the mixtures, the two phospholipids were codissolved in chloroform, and the chloroform was removed first by evaporation, then by vacuum. The resulting dry film was then rehydrated at 50° C., and liposomes were prepared by extrusion through polycarbonate filters at 50° C. Lipid phase transitions were determined with Fourier transform infrared spectroscopy, a method that measures vibrational frequency of the hydrocarbon chains as a function of temperature. An increase in frequency coincides with the phase transition.

Figure 10:
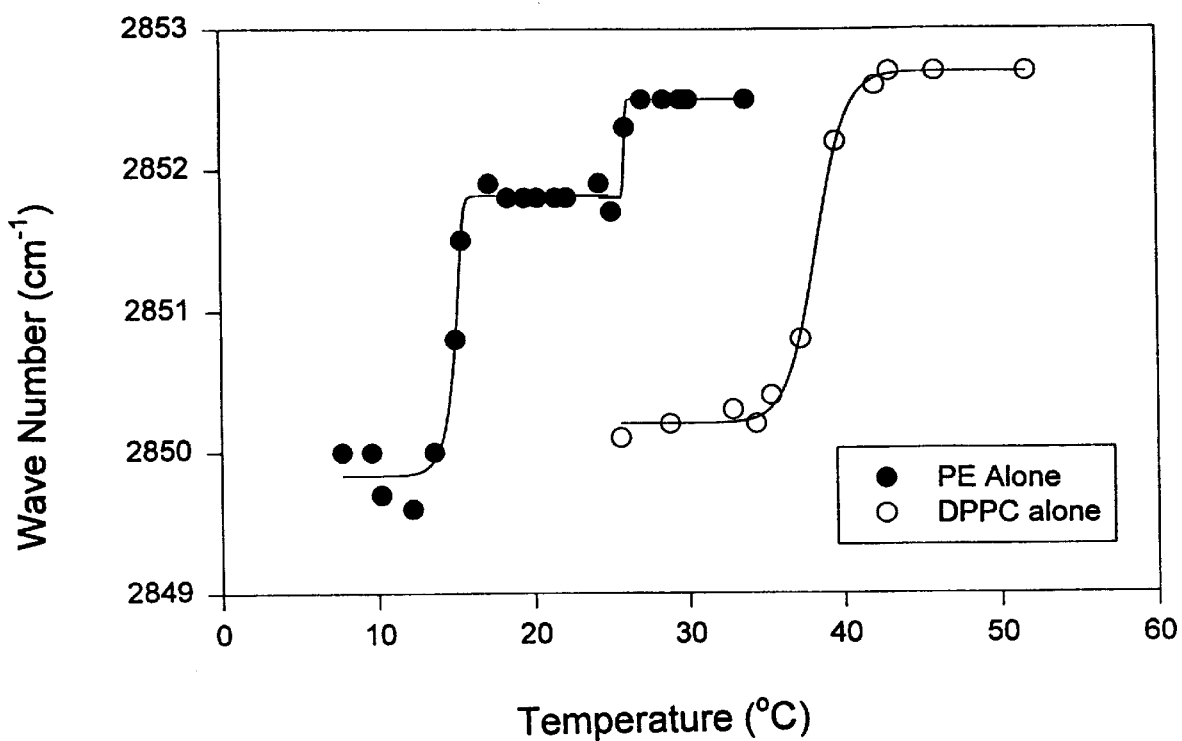
FIG. 10 is a plot of vibrational frequency vs. temperature by Fourier transform infrared spectroscopy, taken individually on two homogeneous liposomes, without antifreeze proteins present.

The frequencies as a function of temperature are shown in FIG. 10 for liposomes formed from the two lipids individually, the filled circles (●) representing the egg PE liposomes and the open circles (○) representing the DPPC liposomes. The two liposomes undergo two distinctly different phase transitions, DPPC showing a phase transition centered at about 42° C., and egg PE showing two phase transitions, one at about 12° C. and another at about 25° C. The two transitions for egg PE are known to correspond to the gel-to-liquid crystalline transition (12° C.) and the bilayer-to-nonbilayer transition (25° C.), respectively.

Figure 11:
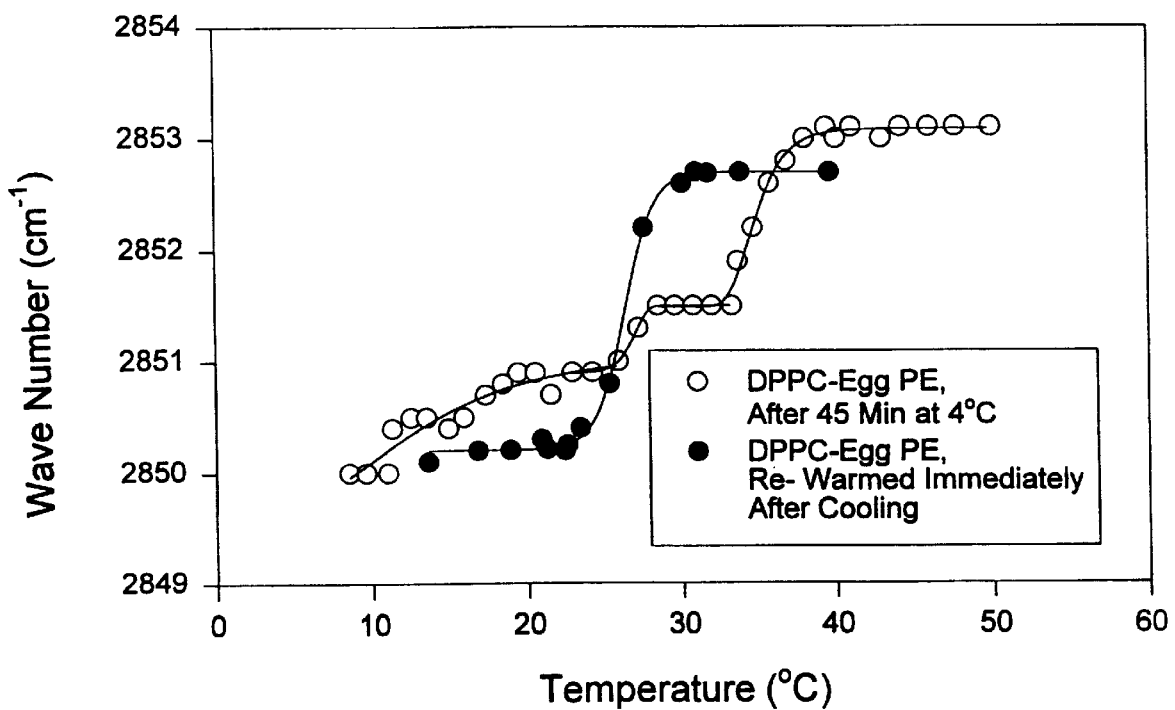
FIG. 11 is a plot similar to that of FIG. 10, except taken on a single heterogeneous liposome, again without antifreeze proteins present.

For the liposomes formed from the mixture of DPPC and egg PE, the results are shown in FIG. 11. The measurements were taken upon rewarming after cooling to 4° C. In one run, represented by the filled circles (●), the rewarming was performed immediately after the cooling, and the liposomes showed a single transition centered at about 25° C. In another run, represented by the open circles (○), where the same liposomes were cooled and then held at 4° C. for 45 minutes prior to rewarming, the single transition was replaced by two discrete transitions that were attributable to the egg PE and DPPC, respectively.

Subsequent studies showed that the phase separation of egg PE and DPPC occurs rapidly and at any temperature below the transition temperature of DPPC. Incubation at room temperature (22° C.) for as little as 15 minutes led to the phase separation. Phase separation of these two phospholipids is irreversible.

EXAMPLE 7

Figure 12:
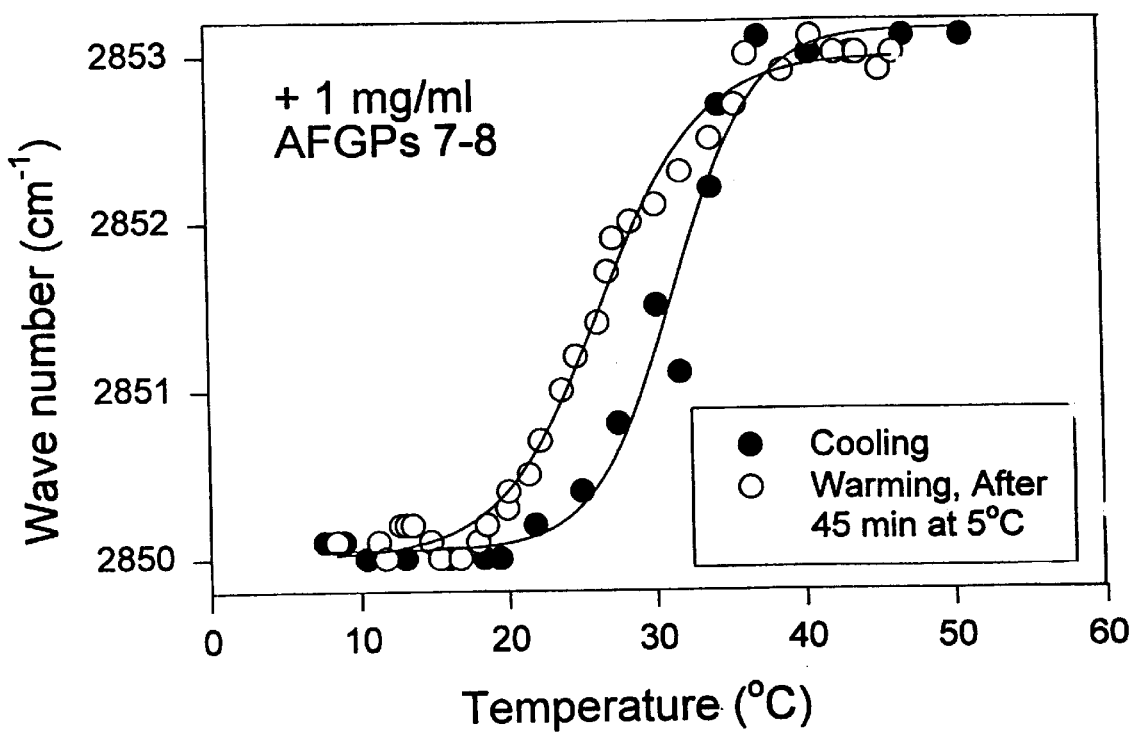
FIG. 12 is a plot similar to that of FIG. 10, taken on a heterogeneous liposome in the presence of antifreeze proteins.

This example illustrates the effect of antifreeze proteins on the lipid phase separations, again as shown by Fourier transform infrared spectroscopy. The lipid composition used in these studies was the same as in Example 6. The antifreeze proteins were 1–2 mg of AFGP Fractions 7–8 from *Dissostichus mawsoni* per mL of liposome suspension, and the results are shown in FIGS. 12 (using 1 mg/mL) and 13 (using 2 mg/mL). AFGPs were added before the samples were cooled.

Figure 13:
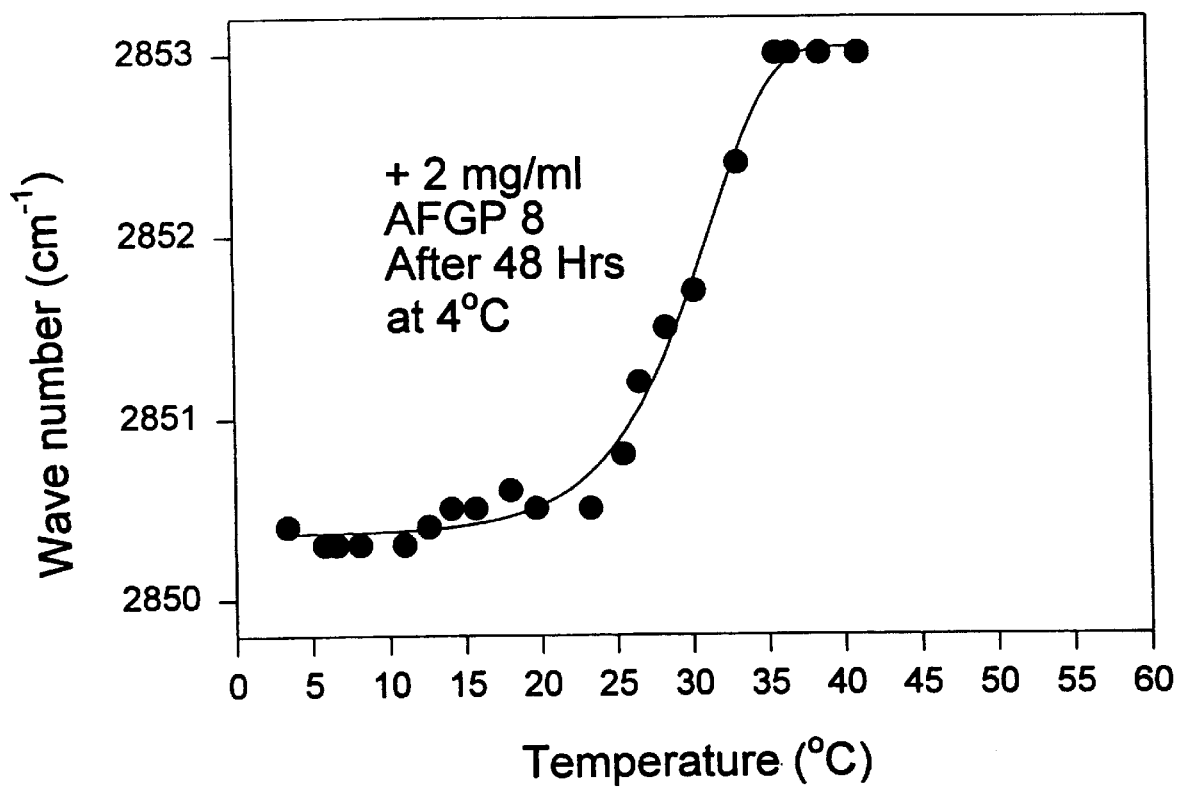
FIG. 13 is a further plot similar to that of FIG. 10, also taken on a heterogeneous liposomes in the presence of antifreeze proteins.

In FIG. 12, the filled circles (●) represent measurements taken during cooling through the transition temperature, and the open circles (○) represent measurements taken during rewarming after the liposomes were held at 5° C. for 45 minutes. In each case, a single transition is observed. In FIG. 13, the filled circles represent measurements taken during rewarming of the liposomes after the liposomes had been held at 4° C. for 48 hours. Again, only a single transition is observed.

The foregoing is offered primarily for purposes of illustration. It will be readily apparent to those skilled in the art that the choice of proteins, proportions, methods of treatment, and other parameters of the invention described herein may be further modified or substituted in various ways without departing from the spirit and scope of the invention.

What is claimed is:

1. A method for the treatment of liposomes containing biologically active substances in the interior of said liposomes to reduce leakage of said biologically active substances during thermotropic phase transitions, said method comprising contacting said liposomes with a leakage-reducing amount of one or more thermal hysteresis proteins to a sufficient degree to effect such reduction in leakage.

2. A method in accordance with claim 1 in which said one or more thermal hysteresis proteins are proteins having the molecular structure of thermal hysteresis proteins isolated and purified from north temperate or Arctic fish species.

3. A method in accordance with claim 2 in which said fish species is a member selected from the group consisting of Antarctic notothenioids, northern ocean gadoids, righteye flounders, cottids and eel pouts.

4. A method in accordance with claim 1 in which said one or more thermal hysteresis proteins are members selected from the group consisting of:
   (a) antifreeze glycoproteins isolated and purified from a member selected from the group consisting of *Pagothenia borchgrevinki, Trematomus borchgrevinki, Trematomus bernachii*, and *Dissostichus mawsoni*;
   (b) Type I antifreeze polypeptides isolated and purified from a member selected from the group consisting of *Pseudopleuronectus americanus* and *Limanda ferruginea*;
   (c) Type II antifreeze polypeptides isolated and purified from *Hemitripterus americanus*; and
   (d) Type III antifreeze polypeptides isolated and purified from a member selected from the group consisting of *Macrozoarces americanus, Rhigophila dearborni* and *Lycodes polaris*.

5. A method in accordance with claim 4 further comprising purifying said proteins by extraction with an organic solvent prior to contacting said liposomes with said proteins.

6. A method in accordance with claim 5 in which said organic solvent is a member selected from the group consisting of ketones and ethers.

7. A method in accordance with claim 5 in which said organic solvent is a member selected from the group consisting of acetone and diethyl ether.

8. A method in accordance with claim 1 in which said one or more thermal hysteresis proteins are members selected from the group consisting of:
   (a) antifreeze glycoproteins isolated and purified from a member selected from the group consisting of *Dissostichus mawsoni* and *Trematomus bernachii*;
   (b) Type I antifreeze polypeptides isolated and purified from *Pseudopleuronectus americanus*;
   (c) Type II antifreeze polypeptides isolated and purified from *Hemitripterus americanus*; and
   (d) Type III antifreeze polypeptides isolated and purified from *Macrozoarces americanus*.

9. A method in accordance with claim 1 in which said one or more thermal hysteresis proteins are antifreeze glycoproteins.

10. A method in accordance with claim 1 in which said one or more thermal hysteresis proteins are antifreeze glycoproteins with about molecular weight 2600.

11. A method in accordance with claim 1 in which said liposomes have lipid components that are phosphatidylcholines.

12. A method in accordance with claim 1 in which said liposomes have lipid components selected from the group consisting of dielaidoylphosphatidylcholine and dimyristoylphosphatidylcholine.

13. A method in accordance with claim 1 comprising incubating said liposomes with an aqueous solution of said thermal hysteresis proteins to form an aqueous suspension of said liposomes.

14. A method in accordance with claim 13 in which said thermal hysteresis proteins comprise from about 0.3 mg/mL to about 30 mg/mL of said suspension.

15. A method in accordance with claim 13 in which said thermal hysteresis proteins comprise from about 1 mg/mL to about 20 mg/mL of said suspension.

* * * * *

UNITED STATES PATENT AND TRADEMARK OFFICE
Certificate

Patent No. 5,869,092

Patented: February 9, 1999

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Lisa M. Hays, John H. Crowe, Lois M. Crowe, Robert E. Feeney, Fern Tablin.

Signed and Sealed this Twenty-Fifth Day of April, 2000.

THURMAN K. PAGE
*Supervisory Patent Examiner,*
Technology Center 1600
Art Unit 1615